United States Patent [19]

Stampwala et al.

[11] Patent Number: 4,578,383

[45] Date of Patent: Mar. 25, 1986

[54] CL 1565 ANTIBIOTIC COMPOUNDS

[75] Inventors: Suresh S. Stampwala, Sterling Heights; James C. French, Ann Arbor; Josefino B. Tunac, Troy; Timothy R. Hurley; Richard H. Bunge, both of Ann Arbor, all of Mich.

[73] Assignee: Warner-Lambert Company, Morris Plains, N.J.

[21] Appl. No.: 627,367

[22] Filed: Jul. 2, 1984

Related U.S. Application Data

[63] Continuation-in-part of Ser. No. 447,544, Dec. 7, 1982, abandoned, which is a continuation-in-part of Ser. No. 439,973, Nov. 8, 1982, abandoned, which is a continuation-in-part of Ser. No. 351,704, Feb. 24, 1982, abandoned.

[51] Int. Cl.[4] .................... C07D 9/09; A61K 31/665; A61K 31/685

[52] U.S. Cl. ........................................ 514/7; 549/222; 544/109; 544/359; 546/207; 548/400

[58] Field of Search ............... 549/222; 544/109, 359; 546/207; 548/400; 514/7

[56] References Cited

U.S. PATENT DOCUMENTS 4,239,751 12/1980 Coronelli et al. .................. 424/118

*Primary Examiner*—Norma S. Milestone
*Attorney, Agent, or Firm*—Jerry F. Janssen

[57] ABSTRACT

Novel phosphorus containing antibiotic compounds that are antitumor agents designated CL 1565-A, CL 1565-B, CL 1565-T and their salts, a process for the production and the method of using said compounds, and pharmaceutical compositions containing various salts of the compounds of the invention alone or in combination with other antitumor agents in the treatment of microbial infections and neoplastic diseases, are provided.

10 Claims, 4 Drawing Figures

CL 1565 ANTIBIOTIC COMPOUNDS

CROSS-REFERENCE TO RELATED APPLICATIONS

This application is a continuation-in-part of copending application Ser. No. 447,544 filed Dec. 7, 1982 (now abandoned) which is a continuation-in-part of application Ser. No. 439,973 filed Nov. 8, 1982 (now abandoned), which is a continuation-in-part of application Ser. No. 351,704 filed Feb. 24, 1982 (now abandoned).

BRIEF DESCRIPTION OF THE DRAWING

In FIG. 1, curve 1 represents the ultraviolet spectrum in methanol; curve 2 represents the ultraviolet spectrum in methanol to which acid has been added; curve 3 represents the ultraviolet spectrum in methanol to which base has been added.

SUMMARY AND DETAILED DESCRIPTION

Figure 1:
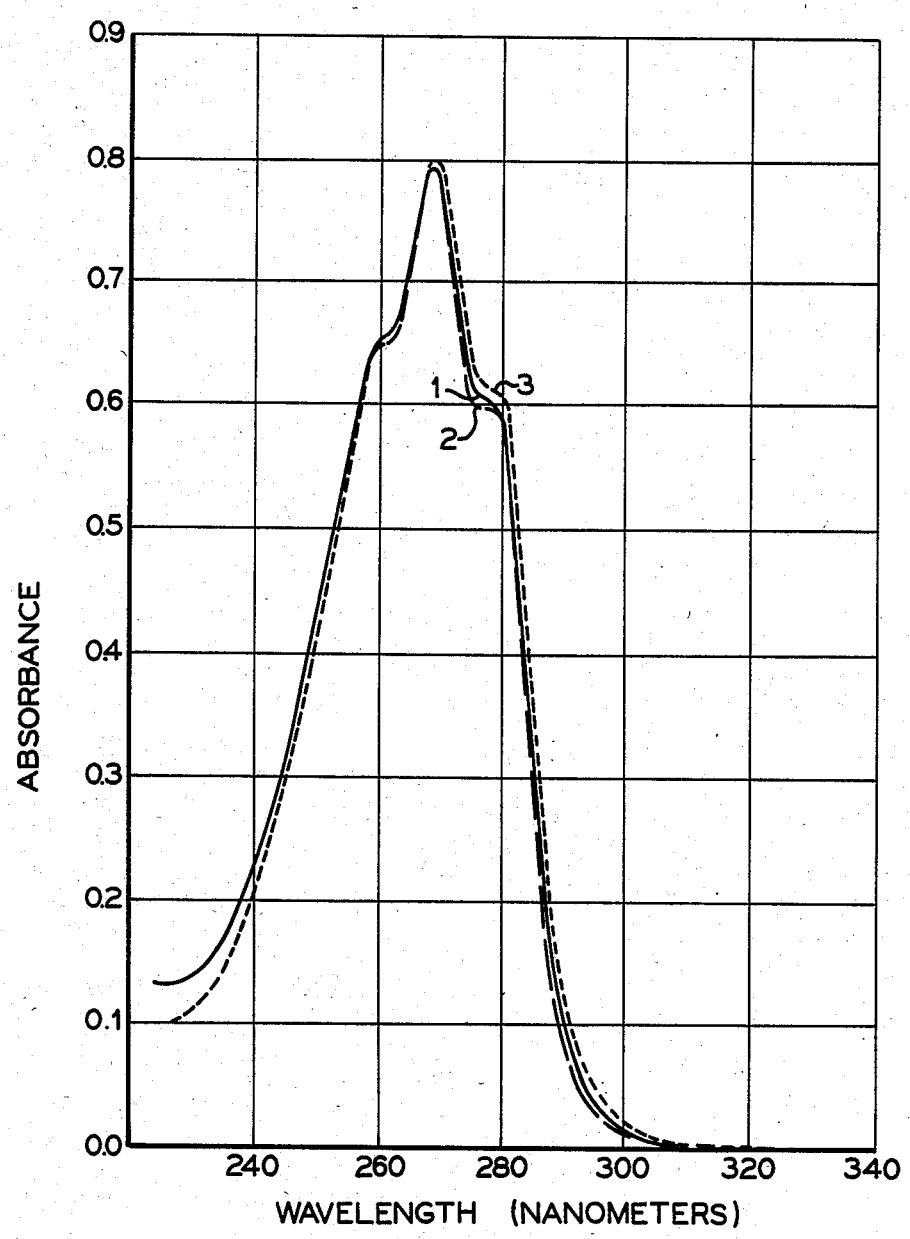
FIG. 1 is ultraviolet spectrum of CL 1565-A.
Figure 2:
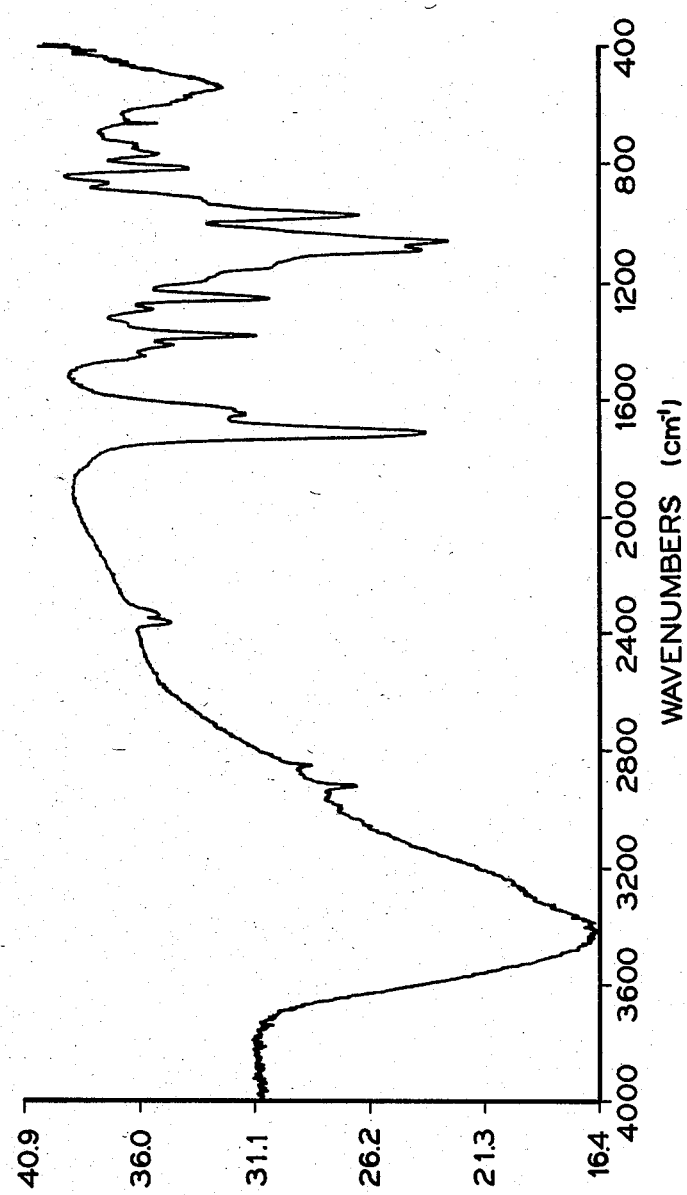
FIG. 2 is the infrared spectrum of CL 1565-A (potassium bromide pellet).
Figure 3:
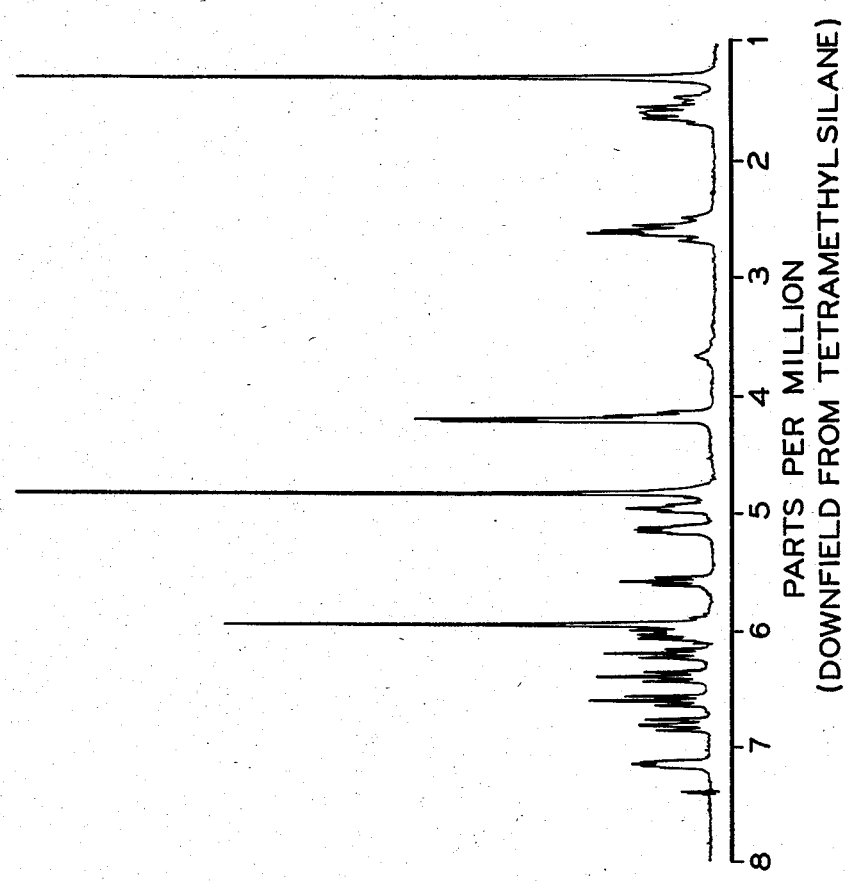
FIG. 3 is the 300 MHz proton magnetic resonance spectrum of CL 1565-A in $D_2O$ solution.
Figure 4:
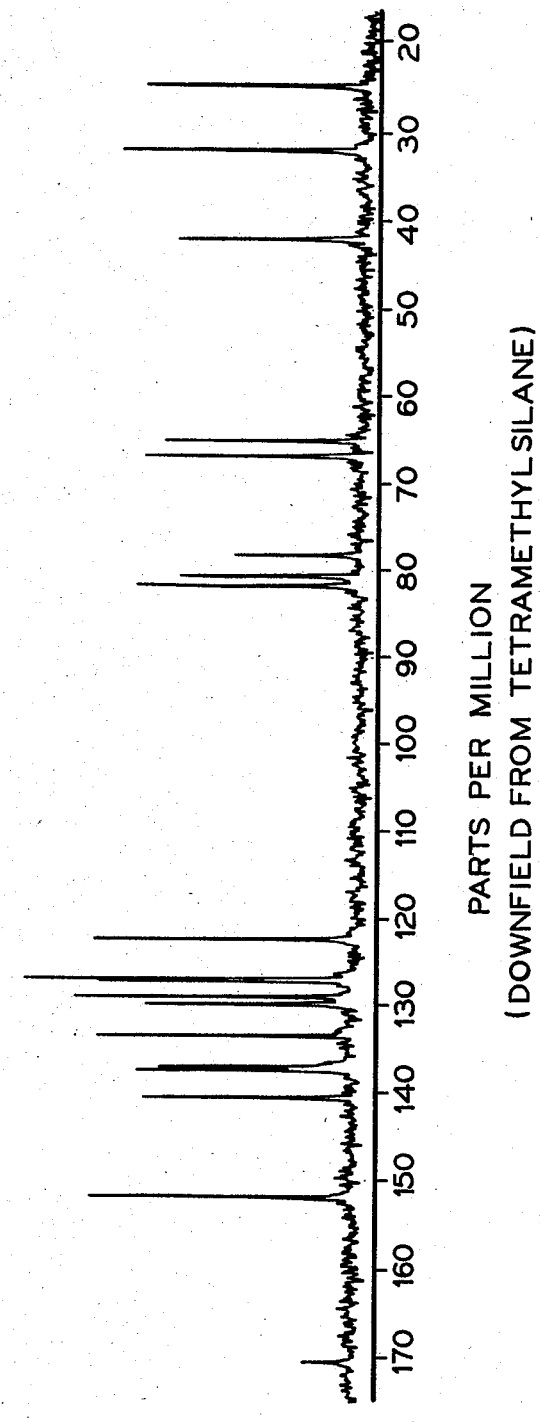
FIG. 4 is the $^{13}C$ nuclear magnetic resonance spectrum of CL 1565-A in $D_2O$ solution.

The present invention relates to novel, phosphorus containing antibiotics that are antitumor agents, designated CL 1565-A and CL 1565-B, and CL 1565-T, and congeners, to pharmaceutically acceptable salts thereof, and to a process for the production and the method of using said compounds. The process, more particularly, relates to a fermentation process using a strain of Streptomyces sp., isolate ATCC 31906, for the production of the said CL 1565 complex of this invention. The structures of three of the CL 1565 antibiotic components, namely CL 1565-A, CL 1565-B, and CL 1565-T, are shown in formulas 1, 2a, and 2b, respectively.

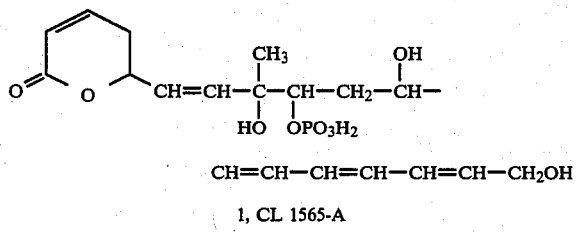

1, CL 1565-A

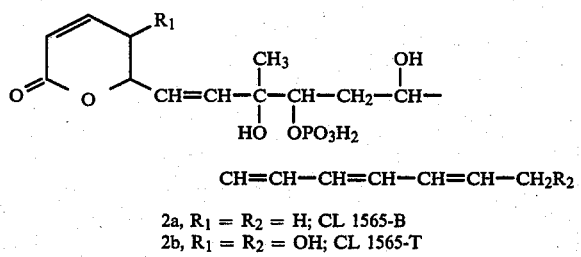

2a, $R_1 = R_2 = H$; CL 1565-B
2b, $R_1 = R_2 = OH$; CL 1565-T

The structural formulas given in 1, 2a, and 2b for CL 1565-A, CL 1565-B, and CL 1565-T, respectively, are the best representations of the structures of these compounds known to the inventors as of the date of filing of this application. These structures were reached by comparison of the physical and spectral characteristics of CL 1565-A, B, and T and some of their derivatives. The results obtained from additional physical measurements, such as those obtained for example, from x-ray crystallography may require future modification of the structures depicted in Formulas 1, 2a, and 2b. Any such possible future refinement of these structural formulas is intended to be included within the scope of the present invention. In addition, the invention relates to pharmaceutical compositions containing various salts of the compounds of the invention alone or in combination with other antitumor agents in the treatment of neoplastic diseases in combination with a pharmaceutically acceptable carrier.

CULTURE CHARACTERIZATION AND FERMENTATION PROCESSES

In accordance with the present invention, CL 1565 compounds are produced by cultivating a selected CL 1565-complex producing strain of a Streptomyces sp., isolate ATCC 31906, under artificial conditions in a suitable nutrient medium until a substantial quantity of CL 1565 compound or compounds (especially CL 1565-A, CL 1565-B, and CL 1565-T) is formed and isolating one or more of the compounds in free acid or salt form.

The strain of Streptomyces suitable for the purpose of this invention was found in a soil sample collected in Sao Paulo, Brazil. This organism was isolated from the soil sample using a suitable agar plating medium. An example of such a medium is one which contains salts such as potassium phosphate, magnesium sulfate, and ferrous sulfate, and carbon substrates such as glycerol and asparagine. The soil was pretreated with calcium carbonate before it was plated on the agar medium and incubated under a favorable temperature, particularly 24° C., to allow the development of the soil microorganisms.

The CL 1565-complex producing organism that was isolated is an unidentified strain of Streptomyces and has been deposited with the American Type Culture Collection, Rockville, Md. 20852, and is being maintained in their permanent culture collection as ATCC 31906. This organism that produces CL 1565-A and its congeners is maintained as a dormant culture in lyophile tubes, cryogenic vials, and in soil tubes at the Warner-Lambert/Parke-Davis Culture Laboratory and is designated as isolate WP-426.

The antitumor compound CL 1565-A and closely related congeners including CL 1565-B and CL 1565-T, are produced by isolate WP-426 during aerobic fermentation under controlled conditions. The fermentation medium consists of sources of carbon, nitrogen, minerals, and growth factors. Examples of carbon sources are various simple sugars such as cerelose, mannose, fructose, xylose, ribose, and glycerol, or other carbohydrate containing compounds such as dextrin, starch, corn meal, and whey. The normal quantity of the carbon sources varies from 0.1 to 10 percent by weight.

The nitrogen sources are organic, inorganic, or mixed organic-inorganic in nature. Examples of such compounds are cotton seed meal, soybean meal, corn germ flour, corn steep liquor, distillers solubles, peanut meal, peptonized milk, and various ammonium salts. The normal amount added varies from 0.1 to 5%, but higher amounts are also acceptable.

The inclusion of minerals and growth factors in the fermentation medium is also helpful in the production of CL 1565-A and its congeners. Examples of media ingredients that provide minerals are potassium phosphate, sodium chloride, ferrous sulfate, calcium carbonate, cobalt chloride, and zinc sulfate. The sources of growth factors include various yeast and milk products.

The preferred method for producing CL 1565-A and its congeners is by submerged culture fermentation. According to an embodiment of this invention, fermentation ingredients are prepared in solution and sterilized by autoclaving or steam heating. The pH of the aqueous medium is preferably between 4 and 8. The fermentation medium is cooled to a suitable temperature, between 16° and 45° C., and then inoculated with the suitable culture. Fermentation is carried out with aeration and agitation, and the maximum production of CL 1565-A and its congeners is usually reached in 2–10 days. Fermentation in solid state can also be used for the production of CL 1565-A and its congeners.

In the submerged culture method, fermentation is carried out in shake flask or in stationary tank fermentors. In shake flasks, aeration is brought about by agitation of the flasks which causes mixing of the medium with air. In the stationary fermentors, agitation is provided by impellers in the form of disc turbines, vaned discs, open turbines, or marine propellers. Aeration is accomplished by injecting air or oxygen into the fermentation mixture.

The examples which follow illustrate the preferred methods by which the products, CL 1565-A and its congeners, are produced. The described processes are capable of wide variation, and any minor departure or extension is considered as within the scope of this invention.

EXAMPLE 1

Seed development and shake flask fermentation.

The culture in its dormant stage is transferred to a CIM-23 agar slant and incubated for 7–14 days at 28° C. A portion of the microbial growth from the slant is used to inoculate an 18×150 mm seed tube containing 5 ml of ARM 1550 seed medium. The seed tube is shaken at 24° C. for 3–4 days.

| CIM 23 agar slant | |
|---|---|
| Amidex corn starch | 10 g |
| N—Z amine, type A | 2 g |
| Beef Extract (Difco) | 1 g |
| Yeast Extract (Difco) | 1 g |
| Cobaltous chloride.6 H₂O | 0.020 g |
| Agar | 20 g |
| Distilled water | 1000 ml |

| 1550 medium | % |
|---|---|
| Bacto-Yeast Extract (Difco) | 0.5 |
| Glucose, Monohydrate | 0.1 |
| Soluble Starch (Difco) | 2.4 |
| Bacto-Tryptone (Difco) | 0.5 |
| Bacto-Beef Extract (Difco) | 0.3 |
| CaCO₃ | 0.2 |

NOTE:
Adjust pH to 7.5 with NaOH before adding CaCO₃

A portion (1 ml) of the microbial growth from the seed tube is transferred to a 300 ml Erlenmeyer baffled shake flask containing 50 ml of SM 64 production medium. The inoculated flask is incubated at 24° C. for 5 days with shaking using a gyratory shaker (2" throw) set at 180 RPM. The fermentation beer after five days of fermentation is tan in color, the mycelia are granular in appearance, and the pH of the fermentation beer is about 5.5.

| SM 64 Production Medium | |
|---|---|
| Whey (Kroger Dairy) | 35.0% by volume |
| Dextrin (Amidex B411), American Maize | 1.5% by weight |
| Pharmamedia (Traders Protein) 431307 | 1.5% by weight |
| Distilled water | |

NOTE:
Adjust pH to 6.5 with sodium hydroxide

The fermentation broth containing CL 1565-A and its congeners is assayed at a 1:100 dilution vs L1210 mouse leukemia cells in vitro. A 0–50% growth of cells compared with an L1210 cell control is considered to indicate activity, with 0% being the most active. The cytotoxicity of two experimental shake flask fermentations were:

| Flask Number | Cytotoxicity (% Growth) | |
|---|---|---|
| | Supernatant | Freeze-dried |
| I | 28 | 14 |
| II. | 17 | 30 |

The above fermentation broths were also tested vs several microorganisms using the agar-disc method. The crude broth was found to be active vs *Neisseria catarrhalis* 03596, *Staphylococcus aureus* 02482, *Bacillus subtilis* 04555, *Kloeckera brevis* M1378, *Rhodotorula glutinis* M1384, *Saccharomyces cerevisiae* 01525, and *Penicillium avellaneum* M2988.

EXAMPLE 2

Fermentation in 200-gallon fermentors.

Seed Development

A cryogenic vial containing approximately 1 ml of culture suspension is used as the source of inoculum. The contents of this cryogenic vial are thawed and aseptically transferred to a two liter, baffled Erlenmeyer flask containing 500 ml of SD-05 seed medium. The inoculated flask is incubated for 46–48 hours at 24° C., on a gyratory shaker, at 130 rpm speed.

| SD-05 Seed Medium | % |
|---|---|
| Amberex 1003 (Amer Labs) | 0.5 |
| Glucose Monohydrate (Cerelose) | 0.1 |
| Dextrin-Amidex B411 (Corn Products) | 2.4 |
| N—Z Case (Humko Sheffield) | 0.5 |
| Spray Dried Meat Solubles (Daylin Labs) | 0.3 |
| CaCO₃ | 0.2 |
| Distilled water | |

After 48 hours, the contents of the seed flask are transferred aseptically to a 30-liter, stainless steel fermentor containing 16 liters of SD-05 seed medium. The inoculated fermentor is incubated for 18–24 hours at 24° C., stirred at 300 RPM, and sparged with air at 1 VVM rate. This microbial growth is used to inoculate the 200-gal production fermentor.

Production Fermentors

A 200-gal fermentor which contains 160 gal of SM 64 is sterilized by heating with steam for 40 min. at 121° C. The medium is cooled to 24° C. and then inoculated with about 16 liters of the microbial growth from the 30-liter seed fermentor. The inoculated medium is allowed to ferment for 5-7 days at 24° C., 190 RPM agitation, and sparged with 1 VVM air. Antifoam agents, Dow Corning "C" and polyglycol P-2000, are used to control foaming.

The production of CL 1565-A and at least two related antitumor antibiotics, namely, CL 1565-B and CL 1565-T, are monitored throughout the fermentation cycle by recording fermentation parameters such as pH and percent sedimentation or growth as well as by in vitro assays vs L1210 mouse leukemia cells and a high pressure liquid chromatographic procedure described later. An example of a fermentation profile in a 200-gal fermentor is shown in the following table.

| Fermentation Time (hr) | pH | % Sedimentation (growth) | % Growth of L1210 Cells | | | Micrograms CL 1565-A/ml (HPLC Assay) |
|---|---|---|---|---|---|---|
| | | | 1:100 | 1:300 | 1:1000 | |
| 0 | 6.0 | 0 | — | — | — | — |
| 12 | 5.8 | 3.6 | — | — | — | — |
| 24 | 5.1 | 13.3 | NA* | — | — | — |
| 36 | 5.15 | 14.7 | NA | — | — | — |
| 48 | 5.35 | 19.3 | NA | NA | NA | — |
| 72 | 5.45 | 22.0 | NA | NA | NA | 3-6 |
| 96 | 5.95 | 24.7 | 18.2 | 52.9 | NA | 10-20 |
| 118 | 7.65 | 43.3 | 0 | 30.2 | NA | 50-65 |
| 132 | 7.80 | 39.3 | 0 | 23.9 | NA | 60-65 |
| 142 | 7.90 | 40.0 | 0 | 17.2 | NA | 60-70 |

NA* = not active

This fermentor was harvested after 142 hours of fermentation with a harvest volume of 140 gal.

EXAMPLE 3

Isolation of CL 1565-A

The harvested beer from the above fermentation was mixed with 34 kg of Celite 545 and filtered through a plate and frame filter press. The filtrate (473 liters) was percolated through a 30.5 cm [O.D.] column containing 120 liters of HP-20 resin (Gillies International, Inc., La Jolla, Calif.). The resin was then washed with water (605 liters), and 90:10 water:methanol (170 liters). Most of the CL 1565-A was then eluted from the resin with 80:20 water:methanol. High pressure liquid chromatographic analyses (HPLC), performed in the manner described below, of the ensuing eluates showed the following elution profile.

| 80:20 water:methanol eluate | grams of CL 1565-A |
|---|---|
| #1 = 340 liters | <2 g |
| #2 = 340 liters | 11.5 g |
| #3 = 340 liters | 7.0 g |

Eluates #2 and #3 were separately concentrated and lyophilized to afford 90.2 g and 78.7 g, respectively, of dark brown solids. These products were combined and dissolved in 3 liters of water. The resulting solution was added to 27 liters of methanol with stirring. After standing overnight at 5° C., the mixture was filtered and the precipitate was washed with 5 liters of methanol. The filtrate and wash were combined, concentrated in vacuo, and lyophilized to yield 104.5 g of a solid. A portion of this product (95 grams) in 1.5 liters of water was added slowly with mixing to 17 liters of 1-propanol. After one hour the resulting mixture was filtered and the precipitate was washed with 2 liters of 1-propanol. The filtrate and wash were combined, concentrated, and lyophilized to afford 57 g of a solid which, by HPLC analysis, contained about 15 g of CL 1565-A.

This product was chromatographed, in approximately 15 g lots, on 1.2 liters of 40 μm $C_{18}$-silica gel (Analytichem International, Inc., Harbor City, Calif.) contained in a 7.6 cm [O.D.] column. The eluent used was 0.005M pH 4.5 ammonium acetate buffer followed by 0.005M pH 4.5 ammonium acetate containing 5% acetonitrile. The fractions collected were assayed by HPLC. The fractions containing CL 1565-A were pooled, concentrated, and lyophilized. A portion (570 mg) of the resulting product was rechromatographed using a Prep LC/System 500 apparatus fitted with a Prep-Pak TM -500/$C_{18}$ column (Waters Instruments, Inc., Milford, Mass.) and 0.1M pH 6.5 phosphate buffer containing 10% acetonitrile as the eluent. The major fractions, containing approximately 375 mg of CL 1565-A, were pooled and concentrated in vacuo. The aqueous solution was passed through a column containing 200 ml of HP-20 resin packed in water. Th resin was then washed with 1400 ml of water and CL 1565-A remaining on the column was eluted with 350 ml of 50% methanol.

EXAMPLE 4

The eluate from the HP-20 resin column of Example 3, containing CL 1565-A, was concentrated in vacuo and passed through a column containing 35 ml of Dowex-50X2 ion exchange resin in the Na+ form. The effluent (pH 5.5) was combined with a water wash of the ion exchange resin column and lyophilized to yield 180 mg of purified CL 1565-A as the sodium salt.

Analysis of this material showed that it contained approximately 1.3 moles of sodium per mole of the parent CL 1565-A acid. The ultraviolet, infrared, 300 MHz proton magnetic resonance, and 13C nuclear magnetic resonance spectra of this material appear in FIGS. 1, 2, 3, and 4, respectively.

The ultraviolet spectrum of CL 1565-A in methanol solution appears in FIG. 1. The solid curve (curve 1) of FIG. 1 shows the ultraviolet spectrum of the monosodium salt of CL 1565-A, prepared as described above in Example 4.

Addition of a trace of acid, such as hydrochloric, sulfuric, or phosphoric acid, to the solution of the monosodium salt of CL 1565-A produces the acid form, the ultraviolet spectrum of which appears in FIG. 1 as curve 2.

Correspondingly, addition of a trace of base, such as sodium hydroxide, produces the dibasic salt of the phosphate moiety of CL 1565-A. The ultraviolet spectrum of this form of CL 1565-A appears as curve 3 in FIG. 1.

The free acid forms of the compounds are somewhat unstable and it is preferred that CL 1565-A, CL 1565-B, and CL 1565-T be isolated as their ammonium salts or as salts of a pharmaceutically acceptable metal or amine cation. Suitable pharmaceutically acceptable salts include inorganic salts of CL 1565-A, CL 1565-B, and CL 1565-T such as the ammonium salt and salts of metals including sodium, potassium, magnesium, calcium, barium, aluminum, zinc, iron and the like. Pharmaceutically acceptable salts of the compounds are also formed from pharmaceutically acceptable organic amine cations.

The term pharmaceutically acceptable amine cation contemplates the positively charged ammonium ion and analogous ions derived from organic nitrogenous bases strong enough to form such cations. Bases useful for the purpose of forming pharmacologically-acceptable non-toxic addition salts of such compounds containing free phosphate groups form a class whose limits are readily understood by those skilled in the art. Merely for illustration they can be said to comprise in cationic form those of the formula:

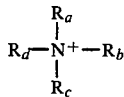

wherein $R_a$, $R_b$, $R_c$ and $R_d$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about two to about four carbon atoms, or monoarylhydroxyalkyl of from about 8 to about 15 carbon atoms or, when taken together with the nitrogen atom to which they are attached, any two of $R_a$, $R_b$, and $R_c$ may form part of a 5 to 6-membered heterocyclic ring containing carbon, hydrogen, oxygen, or nitrogen, said heterocyclic rings and said aryl groups being unsubstituted or mono or dialkyl substituted said alkyl groups containing from about one to about six carbon atoms. Illustrative therefore of $R_a$, $R_b$, and $R_c$ groups comprising pharmacologically-acceptable cations derived from ammonia or a basic amine are ammonium, mono-, di-, tri- and tetramethylammonium, mono-, di-, tri- and tetraethylammonium, mono-, di-, tri- and tetrapropylammonium (iso and normal), ethyldimethylammonium, benzyldimethylammonium, benzyltrimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butyl-monoethanolammonium, tris(hydroxymethyl)-methylammonium, phenylmonoethanolammonium, and the like.

As illustrated in Examples 5 and 6, various salts of CL 1565-A, CL 1565-B, and CL 1565-T are prepared from the sodium salt by passing a solution of the sodium salt through an ion exchange column which has been previously loaded with the desired ion. For example, inorganic salts are prepared by passing an aqueous solution of one of the salts such as the sodium salt, through an ion exchange column such as Dowex-50X1 or Dowex-50X2 which has been previously converted to the salt form by passage of a solution of the chloride salt of the desired metal. Correspondingly, the ammonium salt or organic amine cation salts are prepared in a similar fashion. The ion exchange column is converted to the desired cationic form by passage of ammonium chloride or the chloride salt of the desired organic amine cation through the column. The sodium ion form of CL 1565-A, CL 1565-B, or CL 1565-T is then passed through the column to obtain the desired salt.

The salts of the compounds in accordance with the present invention prepared by either method detailed above contain from about 1.0 to about 2.0 equivalents of cation per equivalent of the parent free acid. By the term "salt" of CL 1565-A, CL 1565-B or CL-1565-T is meant to include compounds having from about one to two molar equivalents of a monovalent cation, such as sodium ion, per molar equivalent of parent free acid, as well as compounds having from about one-half to one molar equivalent of a divalent cation, such as calcium ion, per molar equivalent of the parent free acid.

EXAMPLE 5

A column containing 50 ml of Dowex-50X1 resin in the ammonium ion form was converted to the calcium ion form by passing 200 ml of 0.7M $CaCl_2$ through the column, followed by a water wash of 500 ml.

A solution of 50 mg of the sodium salt form of CL 1565-A contained in 15 ml of water was then passed through the column. Elution with water follwed by lyophilization of the eluate yielded the calcium salt form of CL 1565-A. (%Na=0.00.)

EXAMPLE 6

A column containing 50 ml of Dowex-50X1 resin in the ammonium ion form was converted to the barium ion form by passing 200 ml of 1.0M $BaCl_2$ through the column, followed by a water wash of 500 ml.

A solution of 50 mg of the sodium salt form of CL 1565-A contained in 15 ml of water was then passed through the column. Elution with water followed by lyophilization of the eluate yielded the barium salt form of CL 1565-A. (%Na=0.00.)

EXAMPLE 7

Filtered beer (719 liters), prepared in the same manner as described above, was passed over 31 liters of Dowex-1×2 (chloride form) packed in a 30.5 cm [O.D.] column. The effluent and the subsequent water wash did not contain any detectable amounts of the CL 1565 components. The entire fractionation described herein was monitored by the HPLC method described below using 0.1M pH phosphate buffer ($Na^+$)-acetonitrile (88:12) as the solvent system. The Dowex-1 resin was then eluted with 1M sodium chloride-methanol (1:1) and the eluate was collected in two 10-liter and six 15-liter fractions. Most of the CL 1565-A, CL 1565-B, CL 1565-T, and additional minor CL 1565 components appeared in eluates two through six. These fractions were combined and diluted with 246 liters of acetone. The resulting mixture was stored at 5° C. overnight. The clear supernatant solution was removed and concentrated to 16 liters in vacuo. Lyophilization of this concentrate afforded 800 g of a solid. This product (740 g) was added to 552 g of a similar product isolated in the same manner and the combined solids were dissolved in 20 liters of water. The resulting solution (pH 6.0) was chromatographed on 50 liters of HP-20 resin contained in a 15 cm [O.D.] column. Elution of the HP-20 column with 175 liters of water removed most of the CL 1565-T and all of the minor, more polar CL 1565 components. Most of the CL 1565-A component was eluted with 100 liters of methanol-water (15:85); CL 1565-B and the remaining amount of CL 1565-A were eluted with 83 liters of methanol-water (50:50). The eluates richest in CL 1565-A were combined, concentrated, and lyophilized to afford 123 g of a solid which, by HPLC analysis, contained about 110 g of Cl 1565-A.

A 75-gram portion of this product was dissolved in two liters of 0.05M pH 6.8 phosphate buffer and further purified by chromatography on 52 liters (25 kg) of 100 μm $C_{18}$ reverse phase silica gel (Analytichem International, Inc., Harbor City, Calif.) packed in 0.05M pH 6.8 phosphate buffer ($Na^+$) in a 15 cm [O.D.] column. The column was developed with 0.05M phosphate buffer containing increasing amounts (4.0–6.5%) of acetonitrile. The early fractions contained primarily CL 1565-T and additional minor, more polar CL 1565 components. The majority of the CL 1565-A component was eluted in subsequent fractions. The fractions containing CL 1565-A as the only UV-absorbing component were pooled and concentrated in vacuo to 20 liters. This concentrate was stored overnight at 5° C. and the inorganic salt that precipitated was filtered off. The filtrate was then charged on a 15 cm [O.D.] column containing 28 liters of HP-20 resin. The resin was washed with water (66 liters) and CL 1565-A was then eluted with 42 liters of methanol-water (50:50). The eluates that contained the majority of the CL 1565-A were combined (26 liters), concentrated, and lyophilized to yield 34 g of CL 1565-A containing some inorganic impurities. The inorganic impurities can be removed by dissolving the product in methanol (at 50 to 100 mg/ml), filtering off any insoluble material, and converting the filtrate to an aqueous solution by continually adding water to the filtrate as it is being concentrated in vacuo. Final purification of CL 1565-A is effected by chromatography of the resulting aqueous concentrate on HP-20 resin.

Isolation of Additional CL 1565 Components

Careful chromatography of the concentrates obtained from CL 1565 beers on $C_{18}$-silica gel or HP-20 resin affords fractions that contain CL 1565 components other than CL 1565-A. More than six compounds are detectable by HPLC and are related to CL 1565-A on the basis of similar ultraviolet absorption spectra. Two of these components, namely CL 1565-B and CL 1565-T were isolated as essentially pure compounds. CL 1565 components A, B, and T can be readily distinguished by HPLC on a μBondapak ™ $C_{18}$-silica gel column (3.9 mm I.D.×30 cm) using 0.05M–0.10M phosphate buffers containing varying proportions of acetonitrile at a flowrate of 1.5 ml/min and detection by ultraviolet absorption at 254 nm. Typical retention times of CL 1565-A, B, and T using the above HPLC conditions are given in the following table.

|  | Retention time (min) in: | |
| --- | --- | --- |
|  | Solvent A* | Solvent B** |
| CL 1565-T | 2.8 | <1.5 |
| CL 1565-A | 4.3 | <1.5 |
| CL 1565-B | >15 | 4.2 |

*0.05M pH 7.4 phosphate buffer-acetonitrile (87:13)
**0.05M pH 7.4 phosphate buffer-acetonitrile (78:22)

Crude beers can be assayed in the above manner except the solvent used is 0.1M pH 6.8 phosphate buffer-acetonitrile (88:12). In this case, at a flowrate of 2 ml/min, the retention times of CL 1565-T, CL 1565-A, and CL 1565-B are approximately 2.7, 5.0, and >12 minutes, respectively.

CL 1565-T is eluted earlier than CL 1565-A from HP-20 resin and from reverse phase silica gel. It can be isolated from the early fractions of the $C_{18}$-silica gel column described in example 4, above, using HP-°resin. CL 1565-B is eluted more slowly than CL 1565-A from HP-20 resin and from reverse phase silica gel. CL 1565-B is eluted with 50% methanol during the HP-20 chromatography of the crude Dowex-1 product described in example 4, above. This component can best be isolated by rechromatography on HP-20 followed by chromatography on 40 μm $C_{18}$-silica gel using essentially the same procedure described for the purification of CL 1565-A.

Properties of CL 1565-A, Sodium Salt

Ultraviolet Absorption Spectrum in MeOH (FIG. 1)
λmax 268 nm ($a_1^1$=805) with inflections at 259 and 278 nm
Infrared Absorption Spectrum in KBr (FIG. 2)
Principal absorptions at: 3400, 1710, 1630, 1420, 1387, 1260, 1155, 1090, 1060, 975, 920, 820, and 775 reciprocal centimeters.
Optical Rotation: $[\alpha]_D^{23}$ +28.2° (1.0% in 0.1M pH 7 phosphate buffer)

| Elemental Analysis | % C | % H | % Na | % P |
| --- | --- | --- | --- | --- |
| Calcd. for $C_{19}H_{27.7}O_{10}Na_{1.3}P$: | 47.84 | 5.86 | 6.27 | 6.49 |
| Found: | 48.01 | 5.88 | 6.05 | 6.3 |

Mass Spectrum (via fast atom bombardment) Calcd. for $[C_{19}H_{25}Na_2O_9P+H]^+$ =m/z 475 $[C_{19}H_{26}NaO_9P+H]^+$ =m/z 453 Found: m/z 475, 453
300 MHz Proton Magnetic Resonance Spectrum in $D_2O$ (FIG. 3)
Principal signals at: (s=singlet, d=doublet, t=triplet, m=multiplet) 1.29 s (3H), 1.58 t (1H), 1.70 m (1H), 2.49–2.58 m (2H), 4.13–4.18 m (3H), 4.86 t (1H), 5.09 m (1H), 5.53 t (1H), 5.9–6.0 m (4H), 6.14 t (1H), 6.32 t (1H), 6.55 t (1H), 6.75 dd (1H), and 7.09 m (1H) parts per million downfield from sodium tetramethylsilane (TMS).
$^{13}C$-Nuclear Magnetic Resonance Spectrum in $D_2O$ (FIG. 4)
Principal signals at:

| peak number |  | peak number |  |
| --- | --- | --- | --- |
| 1 | 168.4 | 12 | 79.5 |
| 2 | 149.8 | 13 | 79.0 |
| 3 | 138.1 | 14 | 75.6 |
| 4 | 135.0 | 15 | 64.4 |
| 5 | 134.4 | 16 | 62.7 |
| 6 | 131.3 | 17 | 39.4 |
| 7 | 127.4 | 18 | 29.7 |
| 8 | 126.7 | 19 | 23.5 parts per million |
| 9 | 124.9 |  | downfield from |
| 10 | 124.8 |  | tetramethylsilane |
| 11 | 120.1 |  | (TMS). |

The $^{31}P$-Nuclear Magnetic Resonance Spectrum in $D_2O$ exhibits a doublet (J=10 Hz) at 0.504 ppm downfield from 85% phosphoric acid.
High Pressure Liquid Chromatography
Column: μBondapak ™ $C_{18}$ silica gel (3.9 mm I.D.×30 cm)
Solvent: 0.005M pH 7.3 sodium phosphate buffer-acetonitrile (90:10)
Flowrate: 2 ml/min
Detection: ultraviolet absorption at 254 nm
Retention time: 2.8 min
Antifungal Activity.
Paper disks (12.7 mm in diameter) impregnated with an aqueous solution containing 500 μg of CL 1565-A/ml were placed on a layer of agar inoculated with the indicated microorganisms. After incubation overnight at 28° C., the following zones of inhibition were observed.

| Organism | Zone diameter |
| --- | --- |
| Saccharomyces cerevisiae | 25 mm |
| Saccharomyces italicus | 17 mm |
| Saccharomycoides ludwigii | 25 mm |

In Vitro Activity of CL 1565-A Against L1210 Leukemia Cells
$ID_{50} = 0.078$ μg/ml
In Vivo Antitumor Activity of CL 1565-A Against P388 Lymphatic Leukemia in Mice

| Dose | T/C* × 100 | | |
| --- | --- | --- | --- |
| (mg/kg/day) | test −1 | test −2 | test −3 |
| 25 | — | — | 174 |
| 17 | 256 | 248 | — |
| 12.5 | — | — | 150 |
| 8.5 | 256 | 209 | — |
| 6.3 | — | — | 142 |
| 4.3 | 170 | 172 | — |
| 2.1 | 173 | 157 | — |
| 1.1 | 170 | 139 | — |

The test method used is based on that described in *Cancer Chemother. Reports* 3:1-87 (part 3), 1972.

Properties of CL 1565-T, Sodium Salt

Ultraviolet Absorption Spectrum in MeOH
Nearly identical to FIG. 1 with $a_1 = ^1 774$ at λmax 268 nm and inflections at 260 and 278 nm.
Infrared Absorption Spectrum in KBr
Principal absorptions at: 3400, 1715, 1630, 1380, 1260, 1090, 970, 830 and 770 reciprocal centimeters.
Mass Spectrum (via fast atom bombardment) Calcd. for $[C_{19}H_{25}Na_2O_{10}P+H]^+ = m/z$ 491 Found: m/z 491
360 MHz Proton Magnetic Resonance Spectrum in $D_2O$ The $^1H$-NMR spectrum of CL 1565-T is very similar to the $^1H$-NMR spectrum of CL 1565-A with the exception that the former spectrum exhibits a characteristic one proton signal appearing as a doublet of doublets at 4.34 ppm and is devoid of any signals between 2.2-3.2 ppm downfield from DSS.
Principal Signals of CL 1565-T, sodium salt are at: (s=singlet, d=doublet, t=triplet, m=multiplet) 1.30 s (3H), 1.55-1.64 m (1H), 1.73 t (1H), 4.13-4.20 m (1H), 4.16 d (2H), 4.34 dd (1H), 4.94 t (1H), 5.09 dd (1H), 5.55 t (1H), 5.89-6.06 m (3H), 6.16 m (2H), 6.36 t (1H), 6.56 t (1H), 6.76 dd (1H), 7.14 dd (1H) parts per million downfield from DSS.
90.4 MHz $^{13}C$-Nuclear Magnetic Resonance Spectrum in $D_2O$:

| Peak Number | Chemical Shift* | Peak Number | Chemical Shift* |
| --- | --- | --- | --- |
| 1 | 24.10 | 11 | 126.91 |
| 2 | 41.60 | 12 | 127.18 |
| 3 | 64.68 | 13 | 128.99 |
| 4 | 64.90 | 14 | 133.36 |
| 5 | 66.67 | 15 | 136.87 |
| 6 | 78.28 | 16 | 137.23 |
| 7 | 79.81 | 17 | 142.27 |
| 8 | 84.33 | 18 | 149.46 |
| 9 | 124.40 | 19 | 169.66 |
| 10 | 126.21 | | |

*parts per million downfield from TMS

In Vivo Antitumor Activity of CL 1565-T Against P388 Lymphatic Leukemia in Mice

| Dose mg/kg/day | T/C × 100 |
| --- | --- |
| 25.0 | 157 |
| 12.5 | 147 |
| 6.3 | 142 |
| 3.1 | 147 |

Properties of CL 1565-B, Sodium Salt

Ultraviolet Absorption Spectrum in MeOH
λmax 267 nm ($a_1^1 = 805$) with inflections at 259 and 277 nm
Infrared Absorption Spectrum in KBr
Principal absorptions at: 1720, 1640, 1385, 1200, 1060, 970, and 820 reciprocal centimeters.
360 MHz Proton Magnetic Resonance Spectrum in $D_2O$ Principal Signals at: (s=singlet, d=doublet, t=triplet, m=multiplet) 1.32 s (3H), 1.58 t (1H), 1.72 t (1H), 1.79 d (3H), 2.45-2.68 m (2H), 4.15 t (1H), 4.89 t (1H), 5.10 m (1H), 5.49 t (1H), 5.83-6.21 m (6H), 6.50-6.64 m (2H), 7.06-7.13 m (1H) parts per million downfield from DSS.
90.4 MHz $^{13}C$-Nuclear Magnetic Resonance Spectrum in $D_2O$:

| Peak Number | Chemical Shift* | Peak Number | Chemical Shift* |
| --- | --- | --- | --- |
| 1 | 20.70 | 11 | 127.24 |
| 2 | 25.06 | 12 | 129.47 |
| 3 | 31.91 | 13 | 129.90 |
| 4 | 41.85 | 14 | 134.66 |
| 5 | 66.85 | 15 | 135.94 |
| 6 | 77.87 | 16 | 136.67 |
| 7 | 80.87 | 17 | 140.42 |
| 8 | 81.64 | 18 | 152.01 |
| 9 | 122.41 | 19 | 170.56 |
| 10 | 124.45 | | |

*parts per million downfield from TMS

In Vivo Antitumor Activity of CL 1565-B Against P388 Lymphatic Leukemia in Mice

| Dose mg/kg/day | T/C × 100 |
| --- | --- |
| 25.0 | Toxic |
| 12.5 | 178 |
| 6.3 | 142 |
| 3.1 | 129 |

The antibiotic CL 1565-A and its congeners can be used for their antimicrobial and antitumor activity in the form of pharmaceutical compositions containing any of the various metallic salts such as the sodium, potassium, magnesium, calcium, barium, aluminum, zinc, or iron salt, and the like, or as other salts such as the ammonium salt or salts formed from suitable organic amines. Such pharmaceutical compositions are used with a compatible pharmaceutically acceptable carrier. The compositions may also contain other active antimicrobial and/or antitumor agents. The compositions may be made up in any pharmaceutical form appropriate for the route of administration in question. Examples of such compositions are well known to practitioner of the pharmaceutical art and include solid compositions for oral administration such as tablets, capsules, pills, powders and granules, liquid compositions for topical or oral administration such as solutions, suspensions, syrups and elixirs, and preparations for parenteral administration such as sterile solutions, suspensions, or emulsions.

For use as an antimicrobial agent, the compositions are administered so that the concentration of active ingredient is greater than the minimum inhibitory concentration for the particular organism being treated.

The examples which follow illustrate preferred pharmaceutical compositions containing one or more of the products, CL 1565-A, CL 1565-B, and CL 1565-T, for treatment of diseases, especially neoplastic diseases.

EXAMPLE A

For parenteral use, a sterile, lyophilized product containing in each ampoule 75 mg of CL 1565-A, sodium salt is prepared from the solution of the compound (in injectable distilled water).

EXAMPLE B

CL 1565-A, sodium salt . . . 75 mg
Sodium ascorbate . . . 33 mg

The above components are placed in a sterile vial. An injection is prepared by dissolving the above mixture in a physiological saline solution according to customary procedures. A buffering agent could be added according to need.

EXAMPLE C

CL 1565-A sodium salt (1000 mg) and sodium ascorbate (440 mg) are dissolved in 100 ml of water. The solution is filtered through a sterile filter and aseptically filled into presterilized vials and lyophilized. The vials are sealed under nitrogen with presterilized closures and stored at 5° C. or lower.

Other suitable formulations can be made as described in examples A, B, and C, above, using CL 1565-B and CL 1565-T instead of CL 1565-A. For each of CL 1565-A, CL 1565-B, and CL 1565-T, a suggested dosage regimen for use as an antitumor agent in mammalian species is 1.0–100 mg per square meter for a single daily intravenous treatment course.

What we desire to claim as our exclusive property is the following.

We claim:

1. A phosphorus containing antibiotic compound selected from pharmaceutically acceptable salts of the compounds designated CL 1565-A, CL 1565-B, and CL 1565-T, having the structural formulas 1, 2a, and 2b, respectively,

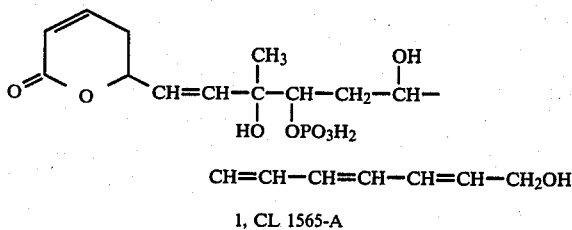

1, CL 1565-A

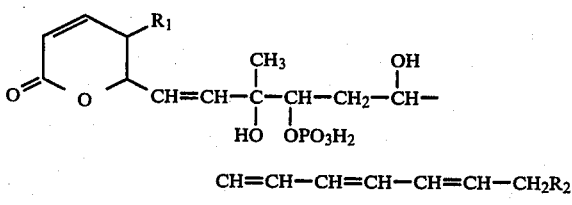

2a, $R_1 = R_2 = H$; CL 1565-B
2b, $R_1 = R_2 = OH$; CL 1565-T

2. A compound according to claim 1 which is a pharmaceutically acceptable salt of CL 1565-A compound.

3. A compound according to claim 1 which is a pharmaceutically acceptable salt of CL 1565-B compound.

4. A compound according to claim 1 which is a pharmaceutically acceptable salt of CL 1565-T compound.

5. A pharmaceutical composition comprising an antimicrobially effective amount of at least one pharmaceutically acceptable salt of CL 1565-A, CL 1565-B, or CL 1565-T, according to claim 1 and a pharmaceutically acceptable carrier.

6. A compound according to claim 1 which is CL 1565-A, sodium salt.

7. A compound according to claim 1 which is CL 1565-B, sodium salt.

8. A compound according to claim 1 which is CL 1565-T, sodium salt.

9. A compound according to claim 1 which is CL 1565-A, calcium salt.

10. A compound according to claim 1 which is CL 1565-A, barium salt.

* * * * *